United States Patent [19]

Tanaka

[11] Patent Number: 5,744,729
[45] Date of Patent: Apr. 28, 1998

[54] SAMPLE SUCKING DEVICE

[75] Inventor: Yosuke Tanaka, Kobe, Japan

[73] Assignee: Toa Medical Electronics Co., Ltd., Hyogo, Japan

[21] Appl. No.: 768,565

[22] Filed: Dec. 18, 1996

[30] Foreign Application Priority Data

Dec. 19, 1995 [JP] Japan .................................. 7-350710

[51] Int. Cl.$^6$ .................................................. G01R 1/16
[52] U.S. Cl. .................................................. 73/864.25
[58] Field of Search .................... 73/864.22–864.25; 422/100; 436/180

[56] References Cited

U.S. PATENT DOCUMENTS

| | | | |
|---|---|---|---|
| 3,748,911 | 7/1973 | Rousselet et al. | 73/864.25 |
| 3,858,450 | 1/1975 | Jones | 422/100 |
| 4,927,603 | 5/1990 | Fischer et al. | 422/100 |
| 5,455,008 | 10/1995 | Earley et al. | 422/100 |

*Primary Examiner*—Robert Raevis
*Attorney, Agent, or Firm*—Greenblum & Bernstein, P.L.C.

[57] ABSTRACT

A sample sucking device, capable of preventing possible malfunction in the automatic sucking operation and protecting against possible risks in the manual sucking operation, which comprises a pipette, an arm, an arm holder, a coiled spring, an up-and-down moving mechanism, a back-and-forth moving mechanism, a first sensor, a second sensor, and a control section. When an abnormal external force exceeding a small preset value is exerted on the pipette or the arm, the arm is forced to pivot at a rotation angle exceeding a preset rotation angle to thereby turn the first sensor OFF. When an external force exceeding a large preset value is exerted on the pipette or the arm, the arm is forced to pivot at a larger rotation angle exceeding the preset rotation angle to thereby turn the second sensor ON. Then, the control section receives an abnormality detection signal from either of the sensors to issue a moving action stop command to the up-and-down moving mechanism or the back-and-forth moving mechanism.

18 Claims, 3 Drawing Sheets

SAMPLE SUCKING DEVICE

BACKGROUND OF THE INVENTION

1. Field of the Invention

The invention relates to a sample sucking device for sucking liquid samples contained in containers. More particularly, the invention relates to a sample sucking device, used in for example an automatic analyzing apparatus, for sucking and collecting liquid samples contained in sample containers for required analysis of the liquid samples.

2. Description of the Related Art

A generally known sample sucking device for sucking liquid samples such as urine or blood comprises a pipette for sucking liquid samples; an arm, having a longitudinal axis extending in a front direction, for holding the pipette substantially vertically; an arm holder for supporting the arm substantially horizontally; an up-and-down moving mechanism for moving the arm in an up-and-down direction; a back-and-forth moving mechanism for moving the arm back-and-forth; and a control section for selectively choosing between an automatic sucking operation and a manual sucking operation.

With this sample sucking device, an automatic sucking operation of samples takes following steps. A container, such as a test tube, in which a sample is fed, is set at a predetermined position forward of the device. Then, the arm is moved forward and is stopped at a predetermined position over the container as set (a front stopping position). And, the arm is lowered to lower the pipette into the container so that the sample can be mixed by suction and discharge and collected in the pipette by suction. The sample collected in the pipette is introduced to a quantifying means such as a sampling valve. Then, after the arm is raised up, it is moved back to and is stopped at a predetermined position (a rear stopping position) over a washing cell such as a washing spit (which is usually incorporated in the device).

Thereafter, the pipette is lowered into the washing cell so as to be washed on the interior and the exterior by discharging a washing liquid from the inside of the pipette and spraying the washing liquid over the outside of the pipette. After the washing of the pipette is completed, the arm is raised up from the washing cell and then is moved forward to return to the front stopping position, for the next suction operation of another sample.

On the other hand, with the sample sucking device, a manual sucking operation of a sample requires an operator to take following steps. The operator, who holds a container in which a sample is fed with his/her hand, puts the container in a position under the pipette supported by the arm which is in the front stopping position and then lifts the container up vertically so that the pipette can be introduced into the container. And, with holding the container in a predetermined level, the operator allows the pipette to collect the sample in the container by suction. After this suction and collection of the sample is completed, the operator lowers the container keeping it in a vertical position so that the pipette can come out of the container. The sequent operations including the quantifying operation and the washing operation are automatically made in the same manner as in the automatic sucking operation.

This conventional type sample sucking device has following disadvantages:

In the automatic suction and collection of samples, if the container has a lid on it, if the container or the washing cell is out of position, or if the pipette is not held in a vertical position, there may arise possible malfunction that the pipette situated in the front stopping position or the rear stopping position may hit the container or washing cell at some part thereof including the side wall, so that it fails to go into the container or washing cell in the normal manner or may be bent, or washing liquid may be spilled out from the washing cell.

In the manual suction and collection of samples, the arm is moved back after the termination of the suction and collection operation. If an operator fails to notice the termination of the suck and collect operation, or if he/she fails to lower the container timely after having noticed the termination, there may be a possible risk that the container and his/her hand holding it may be drawn together into the device with the backward movement of the arm.

The invention has been made to solve the above problems.

SUMMARY OF THE INVENTION

The object of the invention is to provide a sample sucking device capable of preventing possible malfunction in the automatic sucking operation and protecting against possible risks in the manual sucking operation.

According to the invention, there is provided a sample sucking device comprising: a pipette for sucking and collecting liquid samples; a sample sucking means connected to the pipette; an arm, extending in a front direction and pivotally supported at a rear portion or an approximately intermediate portion thereof by a horizontal shaft, for holding the pipette substantially vertically at a front portion thereof; an arm holder for supporting the arm substantially horizontally so that the arm is pivotable in an up-and-down direction; an up-and-down moving mechanism for moving the arm holder in an up-and-down direction; a back-and-forth moving mechanism for moving the arm holder back and forth; at least one sensor, provided on the arm holder, for detecting an abnormal external force exceeding a preset value when exerted on the pipette or the arm; and a control section for controlling actions of the sample sucking means, the up-and-down moving mechanism, and the back-and-forth moving mechanism, wherein the control section further provides a moving action stop command to the up-and-down moving mechanism or the back-and-forth moving mechanism when the sensor detects the abnormal external force.

DETAILED DESCRIPTION OF THE PREFERRED EMBODIMENT

Figure 1:
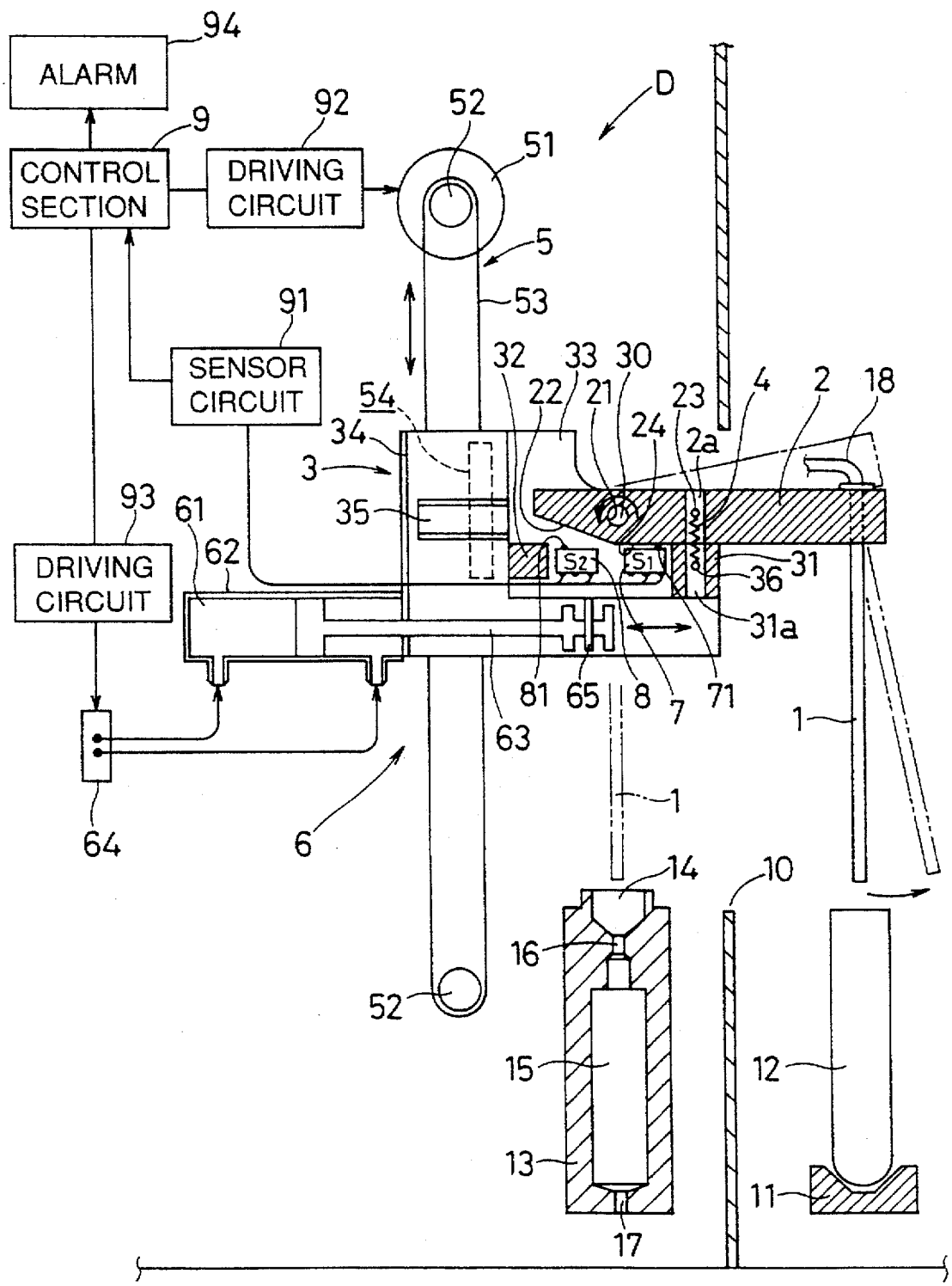
FIG. 1 is a schematic diagram of construction of the sample sucking device according to one embodiment of the invention.

Sample containers of various size, shapes, and materials may be used for storing liquid samples such as urine or blood. As an example of the containers, what is called a tapered test tube is available in which a liquid sample of urine or blood of the order of 5–10 milliliter is stored.

The pipette used may be made of stainless steel or plastics. As the arm and the arm holder, known ones are available. The arm holder may be provided with a stopper for restricting the up-and-down pivoting motion of the arm within a predetermined angle range.

The up-and-down moving mechanism includes for example an elevating belt mounted on the arm holder and stretching between an upper pulley and a lower pulley, and a motor for rotatively driving one of the pulleys.

The back-and-forth moving mechanism includes for example an air cylinder, with the longitudinal axis thereof being oriented in a front direction, and a compressed-air supplying solenoid valve for driving a piston of the air cylinder forward and backward.

The arm holder may be provided with at least one sensor for detecting an abnormal external force exceeding a preset value when exerted on the pipette or the arm, which may cause the aforesaid possible malfunction in the automatic sucking operation or the aforesaid possible risk in the manual sucking operation. Preferably, there are provided a first sensor and a second sensor. In that case, the first sensor and the second sensor may desirably be located at such positions under or over the arm at the arm holder that they can detect the up-and-down pivoting motion of the arm. The first sensor detects a relatively small up-and-down pivoting motion of the arm. In other words, the first sensor detects an abnormal external force exceeding a small preset value exerted on the pipette or the arm. The second sensor detects a relatively large up-and-down pivoting motion of the arm. In other words, the second sensor detects an abnormal external force exceeding a large preset value exerted on the pipette or the arm.

Desirably, the sample sucking device of the invention further comprises an urging means, interposed between the arm and the arm holder, for urging the arm and the arm holder so as to be drawn together. For example a coiled tension spring may be used as a urging means. The urging force of the urging means can be determined, as needed, so that the arm cannot be pivoted until a larger external force acting in an opposite direction to the urging means is exerted on the pipette or the arm.

The control section controls various operations of the sample sucking device of the invention. The control section may include a program to selectively choose between the automatic sample sucking operation (sampler mode) and the manual sample sucking operation (manual mode). In the case of using two sensors, the control section is so connected to the first sensor and the second sensor that it can selectively receive an abnormality detection signal from one of the sensors and give a moving action stop command to the up-and-down moving mechanism or the back-and-forth moving mechanism.

A micro switch, a photo interrupter, and the like may be selectively chosen for the first and second sensors, as needed. It will be appreciated that more than two sensors may be used. For example, in a case where there are provided three sensors of the first, second and third sensors, the abnormal external force can be detected in three levels, large, medium, and small, by those sensors, and accordingly the control section can issue the moving action stop command in a further precise manner.

It is further desirable that the control section is so constructed that after having given the moving action stop command to the up-and-down moving mechanism or the back-and-forth moving mechanism, it can issue an additional command to stop further operations on the suction and discharge of the sample and the washing of the pipette. This can further ensure that the possible malfunction in the automatic sucking operation or the possible risk in the manual sucking operation is prevented.

Preferably, the sample sucking device of the invention may comprise a visible alarm issuing means such as a LED lamp and an audible alarm issuing means such as a buzzer. In that embodiment, in the automatic suction operation of the sample or the manual suction operation of the sample, when the control section receives any abnormality detection signal from the first sensor or the second sensor, the control section issues the moving action stop command to the up-and-down moving mechanism or the back-and-forth moving mechanism, together with a command to issue the alarm to the visible alarm issuing means and/or the audible alarm issuing means.

Concrete Embodiment of the Invention

Referring now to the accompanying drawings, the embodiment of the invention will be described below. It is to be understood, however, that the scope of the invention is by no means limited to the following embodiment.

FIG. 1 is a schematic diagram of construction of the sample sucking device according to one embodiment of the invention. In FIG. 1, a sample sucking device D is constructed mainly of a pipette 1, an arm 2 for holding the pipette 1, an arm holder 3 for supporting the arm 2, a coiled spring 4 as an urging means, an up-and-down moving mechanism 5 for the arm 2, a back-and-forth moving mechanism 6 for the arm 2, a first sensor 7 and a second sensor 8 both mounted on the arm holder 3, and a control section 9.

The pipette 1 is made of stainless steel and is for use in making the suck-and-discharge mixing of liquid samples, such as stock urine, fed into a test tube 12, as well as the suction and collection of the same. The pipette 1 is a capillary tube having an inner diameter of 0.7 mm and an outer diameter of 2.0 mm and insertable in the test tube 12 as was carried to a sample collecting position. The sample collecting position is set to a location forward of a front opening 10 formed on the front of the device D (the right side of FIG. 1). The test tube 12 is carried to the sample collecting position standing upright on a rack 11. A top portion of the pipette 1 is connected to a sample suction motor as a sample sucking means, not shown, through a tube 18. A washing spit 13 is provided at a location rearward of the front opening 10 of the device D.

The spit 13 is constructed mainly of a washing portion 14 having a mouth at the top and a waste liquid storage portion 15 having substantially the same diameter as the washing portion 14. The washing portion 14 has a lower portion which is tapered down toward the bottom. The washing portion 14 opens into the large diameter waste liquid storage portion 15 through a small diameter tubular portion 16 into which the pipette 1 can be inserted from the bottom of the washing portion 14. Further, the bottom of the waste liquid storage portion 15 opens into a discharge port 17 connected to a waste liquid reservoir not shown. The washing portion 14 has an injection port not shown at the rear side as viewed in FIG. 1. The injection port opens in the washing portion 14 so that the exterior of the pipette 1 inserted in the waste liquid storage portion 15 can be washed. A washing fluid used is a mixture of a compressed washing liquid (0.5 kg/cm$^2$) and a compressed air (0.5 kg/cm$^2$) mixed in a prescribed proportion or either of the fluids. The compressed washing liquid and the compressed air are supplied from a fluid supplying device not shown.

The arm 2 is a rectangular parallelepiped member having a longitudinal axis extending laterally as viewed in FIG. 1. A top end portion of the pipette 1 is fixed to a front end portion of the arm 2 (the right side of FIG. 1) so that the pipette 1 can be held in a vertical position at substantially a right angle to the longitudinal axis of the arm 2. A horizontal pin hole 21 is formed in the arm 2 on the rear end side of the center of the same. A pin 30 as a horizontal shaft, which is planted in a slider 33 of the arm holder 3, is inserted in the pin hole 21. Thus, the arm 2 is supported on the pin 30 so that it can pivot around the pin 30 in a up-and-down direction reciprocally. Under the arm 2, a front stopper 31 and a rear stopper 32 are fixedly mounted to the slider 33 along the longitudinal axis of the arm 2.

The front stopper 31 is directly under the arm 2 between the mounting portions of the pin 30 and the pipette 1 and abuts on a generally horizontal surface formed on the back surface of the arm 2. Thus, the pipette 2 is permitted to be held in substantially a vertical position. The rear stopper 32 is directly under a rear end portion of the arm 2 and is able to abut on an inclined surface 22 (a second detecting surface mentioned later) formed on the rear portion of the arm 2. Thus, the arm 2 is permitted to pivot within a small rotation angle range defined between the front stopper 31 and the rear stopper 32.

Further, the front stopper 31 and a body of the arm 2 on the front stopper 31 are provided with a vertical through-hole 31a and a vertical through-hole 2a, respectively. The coiled spring 4, which acts to draw the arm 2 and the front stopper 31 together, is interposed between the both through-holes 31a, 2a. An upper end of the coiled spring 4 and a lower end of the same are respectively fixed to a retaining pin 23 formed on an inside wall of the through-hole 31a and a retaining pin 36 formed on an inside wall of the through-hole 2a, so as to urge the front portion of the arm 2 downward.

The slider 33 of the arm holder 3 is movable horizontally along a linear guide 35 mounted on a holder body 34. Under the holder body 34, an air cylinder 61 as the back-and-forth moving mechanism 6 is located.

The air cylinder 61 is constructed mainly of a cylinder 62, a piston 63, a solenoid valve 64 for regulating compressed air injected into the cylinder 62, and a shifter 65 fixed to a front portion of the piston 63. The shifter 65 connects a rod of the piston 63 with the slider 33 so that a back-and-forth reciprocating motion of the piston 63 can be transmitted to the slider 33.

This constructed back-and-forth moving mechanism 6 allows the arm 2 to be so shifted between the front stopping position and the rear stopping position that the pipette 1 can be selectively shifted between a position over the sample collecting position and a position over the washing spit 13.

The arm holder 3 and the back-and-forth moving mechanism 6 are connected to the up-and-down moving mechanism 5. The up-and-down moving mechanism 5 is constructed mainly of a motor 51 mounted on a frame of the device D, a pair of pulleys 52, an elevating belt 53, and a shifter 54 joining the holder body 34 and the elevating belt 53 together. One of the pair of pulleys 52 is connected to a motor shaft 51 and the other of the pulleys 52 is located under the motor shaft 51.

This constructed up-and-down moving mechanism 5 allows the arm 2 to be so shifted vertically that the pipette 1 can be selectively shifted between the front stopping position and the sample collecting position under the front stopping position and between the rear stopping position and the sample discharging position in the washing spit 13 under the rear stopping position.

In the sample sucking device D, the suck collection operation can be selectively switched between the automatic mode and the manual mode.

In the automatic mode, a selected test tube 12 in which a sample is fed is carried to the sample collecting position via the rack 11. Then, the arm 2, which is on standby at the front stopping position over the set test tube 12, is lowered to allow the pipette 1 to enter the test tube 12 so as to suck and collect the sample in the pipette 1. Then, the arm 2 is raised up and then is moved back to a position over the washing spit 13. Then, the arm 2 is lowered to allow the pipette 1 to enter the washing spit 13 so as to wash the pipette 1.

In the manual mode, an operator holds with his/her hand a selected test tube 12 or an "interrupted" test tube 12 brought in from another place in the middle of the operation in the automatic mode. Then, he/she lifts the test tube 12 until the pipette 1 at the arm 2, which is at rest at the front stopping position over the sample collecting position, is inserted in the test tube 12 into such a level that the pipette 1 can draw up the sample in it. The arm 2 is kept still in that position for some seconds or until a command from the operator is entered. Then, the suction and collection operation takes effect. After completion of the suction and collection operation of the sample, the operator lowers the test tube 12 to draw it out from the pipette 1. Then, the arm 2 is moved back to a position over the washing spit 13 and then is lowered to allow the pipette 1 to enter the washing spit 13 so as to wash the pipette 1.

The first sensor 7 and the second sensor 8 are placed on a lower portion of the slider 33 between the front stopper 31 and the rear stopper 32. The both sensors are positioned directly under the arm 2. Each of the first sensor 7 and the second sensor 8 is constructed of a micro switch having a plunger 71, 81 respectively at the top. First detecting surface 24 formed on the back surface of a front portion of the arm 2 at the right side of the pin 30 is capable of exerting pressure on plunger 71. Second detecting surface 22 (an inclined surface) formed on the back surface of a rear portion of the arm 2 at the left side of the pin 30 is capable of exerting pressure on plunger 81.

When the front stopper 31 is in contact with the arm 2, in other words, when no external force exceeding a preset value A acts on the arm 2, the plunger 71 is pressed by the first detecting surface 24 to close contact points (ON) inside the sensor 7. When an external force exceeding the preset value A acts on the arm 2, the arm 2 is forced to pivot and thereby move away from the first detecting surface 24 to open the contact points (OFF) inside the sensor 7.

On the other hand, when no external force exceeding a preset value B acts on the arm 2, the plunger 81 is kept a distance from the second detecting surface 22 to close contact points (OFF) inside the sensor 8. When an external force exceeding the preset value B acts on the arm 2, the arm 2 is forced to pivot and thereby the plunger 81 is pressed by the second detecting surface 22 to open the contact points (ON) inside the sensor 8. The first sensor 7 and the second sensor 8 are connected to an input section of a sensor circuit 91. The "ON" and "OFF" in the first sensor 7 and the second sensor 8 are associated with the signal receiving state of the sensor circuit 91 which the signals from each of the sensors 7, 8 are entered.

An external force exerted on the arm 2 is an external force which acts on the pipette 1 or the front portion of the arm 2 so that the arm 2 can be forced to pivot upward around the pin 30 against an urging force of the spring 4. A relationship between the preset values A and B is A<B. The preset value A is set on the assumption of a small fixed external force exerted on the arm 2 in an axial direction of the pipette 1 by the arm 2 starting on the downward movement from the front stopping position or the rear stopping position or being in the middle of the downward movement. The preset value B is set on the assumption of a large fixed external force exerted on the arm 2 in a direction intersecting at substantially a right angle to the axis of the pipette 1 by the arm 2 starting on the backward movement from the front stopping position or being in the middle of the backward movement.

The control section 9 includes a microcomputer including CPU, ROM, RAM, timer, counter, and the like. To the control section 9 are connected an output section of the sensor circuit 91, input sections of driving circuits 92, 93 for the up-and-down moving mechanism 5 and the back-and-forth moving mechanism 6, input sections of alarm driving circuits 94 for a LED lamp as a visible alarm issuing means and a buzzer as an audible alarm issuing means, and other input and output sections not shown.

Figure 2:
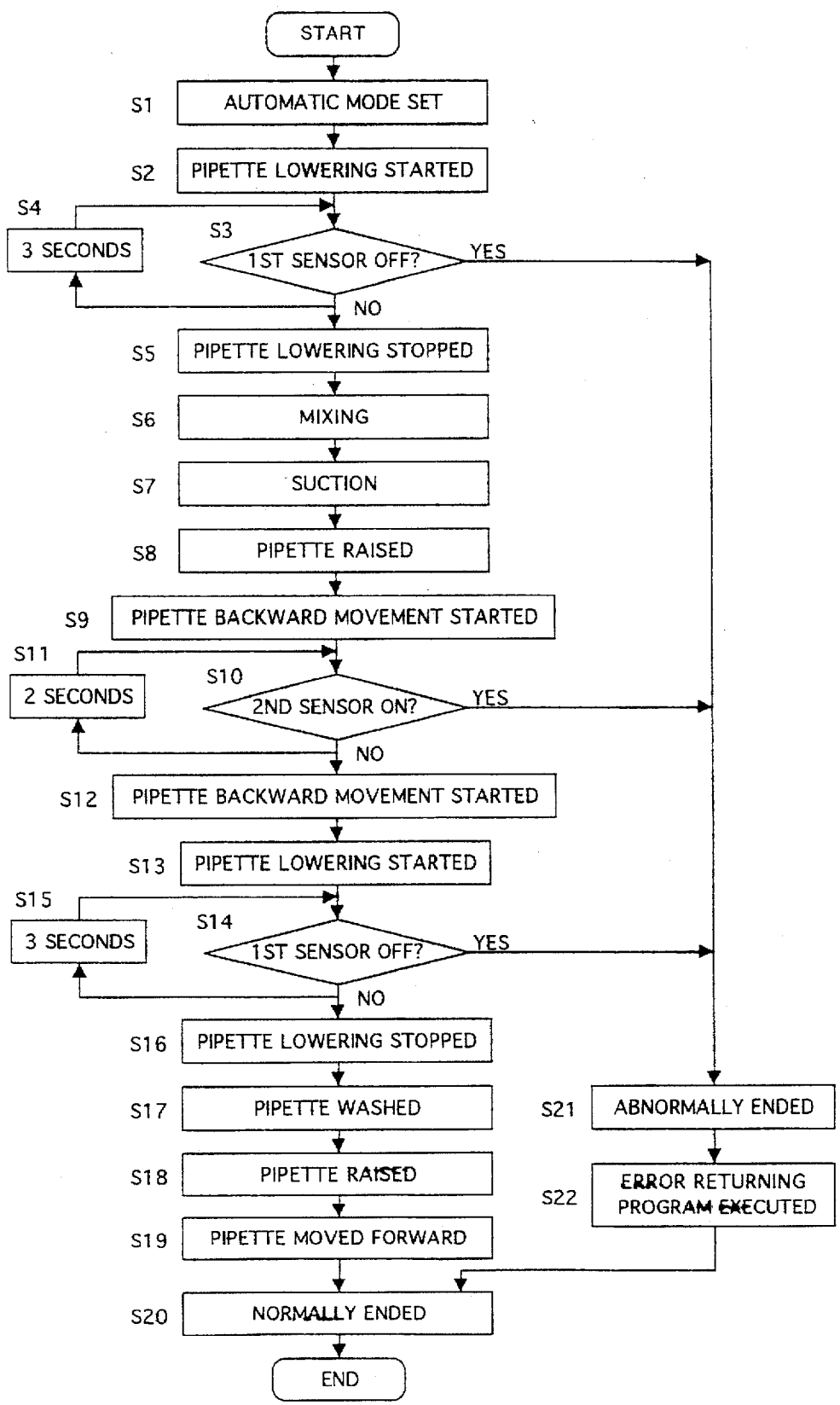
FIG. 2 is a flowchart showing various kinds of operations for making automatic sucking operation in the sample sucking device of FIG. 1.
Figure 3:
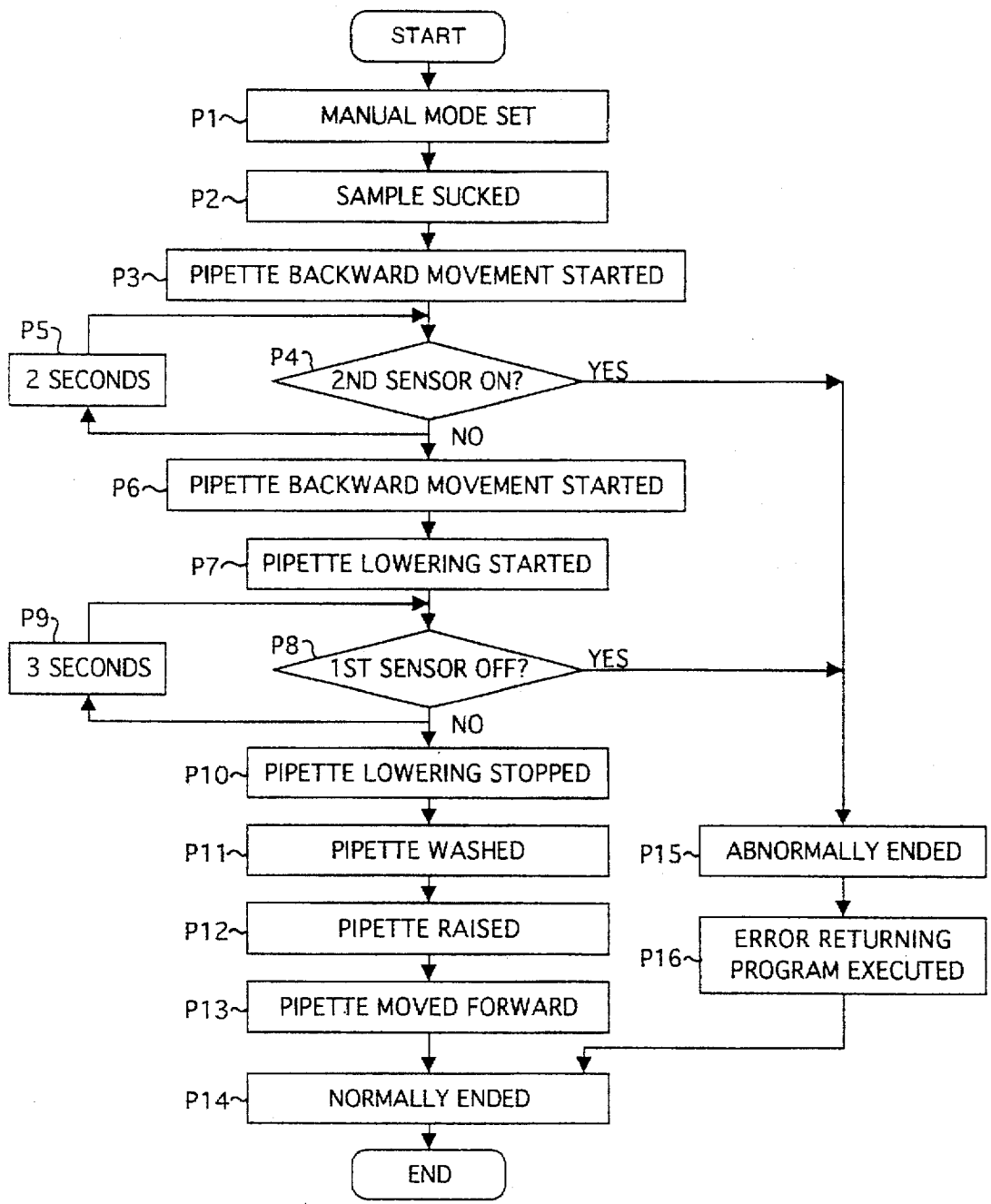
FIG. 3 is a flowchart showing various kinds of operations for making manual sucking operation in the sample sucking device of FIG. 1.

Next, with reference to the flowcharts of FIGS. 2 and 3, operations of the sample sucking device D will be described below. The operations of the sample sucking device D are all controlled by the abovesaid controlling section.

The suction and collection of samples in the automatic mode will be described with reference to the flowchart of FIG. 2. In steps S1–S4: First, the device is set in the automatic mode (Step S1). When the sample sucking device D starts on operation, the pipette 1, which is in the initial position over and outside the test tube 12 upright on the rack 11 or the front stopping position, is lowered at a constant speed into the test tube 12 (Step S2). At this time, if an external force exceeding the preset value A is exerted on the pipette 1, the plunger 71 of the first sensor 7 comes to be away from the first detecting surface 24 to open the contact points (OFF) inside the sensor 7. This operation is supervised for three seconds (Steps S3, S4). If the control section receives any abnormal signal during the supervision, it decides that some abnormal condition is encountered in the lowering motion of the pipette 1 and issues a moving action stop command to the up-and-down moving mechanism 5, together with a command to drive the LED lamp and the buzzer and further a command to stop further operations on the mixing of the selected sample and the suction and discharge of the sample and the washing of the pipette 1 (Step S21). After that, an error returning program is executed (Step S22). The error returning program in this case can select the return of the pipette 1 to the initial position.

In steps S5–S12: First, the pipette 1, which was in the front stopping position, is stopped lowering after 3.0 seconds passed from the start on the lowering motion and is kept in the sample collecting position (Step S5). And, a suck and discharge operation of the pump 4 is performed and thereby the suck-and-discharge mixing of the sample is performed by the pipette 1 five times every 1.0 second (Step S6). Then, after the control section performs a required valve open-and-close operation, it drives a sample suction pump to perform the suction operation. This in turn causes the sucking operation of the pipette 1, so that a 2.0 milliliter of sample is drawn up in the pipette 1 from the test tube 12. The sucked sample is introduced into a sampling valve for quantification (Step S7).

Then, after the pipette 1 is raised up (Step S8), the arm 2 is moved back at a constant speed from the front stopping position to the rear stopping position over the washing spit 13 (Step 9). At this time, if an external force exceeding the preset value B is exerted on the pipette 1, the plunger 81 of the second sensor 8 is pressed by the second detecting surface 22 to open the contact points (ON) inside the sensor 8. This operation is supervised for two seconds (Steps S10, S11). If the control section receives any abnormal signal during the supervision, it decides that some abnormal condition is encountered in the backward motion of the pipette 1 and issues a moving action stop command to the back-and-forth moving mechanism 6, together with a command to drive the LED lamp and the buzzer and further a command to stop further operations on the discharge of the selected sample and the washing of the pipette 1 (Step S21). After that, an error returning program is executed (Step S22). The error returning program in this case can select the discharge of the sucked sample from the pipette 1, the washing of the pipette 1, and the return of the pipette 1 to the initial position. The pipette 1 which was in the front stopping position is stopped moving backward after 2.0 seconds passed from the start of the backward movement and is kept in the rear stopping position (Step S12).

In steps S13–S16: the pipette 1 which was in the rear stopping position is lowered at a constant speed into the washing spit 13 (Step S13). At this time, if an external force exceeding the preset value A is exerted on the pipette 1, the plunger 71 of the first sensor 7 comes to be away from the first detecting surface 24 to open the contact points (OFF) inside the first sensor 7. This operation is supervised for three seconds (Steps S14, S15). If the control section receives any abnormal signal during the supervision, it decides that some abnormal condition is encountered in the lowering motion of the pipette 1 and issues a moving action stop command to the up-and-down moving mechanism 5, together with a command to drive the LED lamp and the buzzer and further a command to stop further operations on the discharge of the sucked sample and the washing of the pipette 1 (Step S21). After that, an error returning program is executed (Step S22). The error returning program in this case can select the discharge of the sucked sample from the pipette 1, the washing of the pipette 1, and the return of the pipette 1 to the initial position. The pipette 1 which was in the rear stopping position is stopped moving downward after 4.0 seconds passed from the start of the lowering motion and is held in the sample discharging position (Step S16).

In steps S17–S20: First, a washing liquid, delivered into the pipette 1 placed in the sample discharging position in the washing spit 13, is discharged together with a residual sample into the waste liquid storage portion 15 and thereby the interior of the pipette 1 is washed (Step S17). Further, the aforesaid washing fluid is fed into the washing portion 14 to wash the exterior of the pipette 1. The discharged liquid to the waste liquid storage portion 15 is discharged from the discharge port 17 to the waste liquid reservoir.

Thereafter, the pipette 1 is raised from the sample discharging position (Step S18). Then, the arm 2 is moved forward at a constant speed from the rear stopping position to the front stopping position over another test tube 12 in which another sample is fed (Step S19). And, the operation goes to Step S20.

The suction and collection of samples in the manual mode will be described with reference to the flowchart of FIG. 3. In steps P1–P3: First, the sample sucking device D is set in the manual mode (Step P1) and starts on operation. In the manual mode, the arm 1 is held in the front stopping position and thus the pipette 1 is in the initial upward position. An operator lifts a selected test tube 12 until the pipette 1 is inserted in the mouth of the test tube 12 in an appropriate level and holds the test tube 12 in that level. Then, the suction and collection of the sample is effected at an operation command entered by the operator (Step P2). After the suction and collection of the sample is performed for a required time, the operator lowers the test tube 12 so that the pipette 1 can be drawn out of the mouth of the test tube 12. Then, at an operation command entered by the operator, the arm 2 is forced to move back at a constant speed from the front stopping position to the rear stopping position over the washing spit 13 (Step P3).

The operations made at following steps P4–P16 in the manual mode are identical to those made at steps S10–S22 in the aforesaid automatic mode. Due to this, the detailed description thereon is omitted.

In this sample sucking device D, the first sensor 7 and the second sensor 8 are capable of detecting an abnormal external force exerted on the pipette 1 or the arm 2 at two different levels in strength. This enables the pipette 1 to be prevented from being damaged by presetting the external forces expected in the moving action of the pipette 1.

Further, in this sample sucking device D, the arm 2 is permitted to be stopped acting immediately, not only when a large abnormal external force is exerted on the arm 2 but also when a small abnormal external force is exerted on the arm 2. Thus, the pipette 1 and the driving sources of the up-and-down moving mechanism 5 and the back-and-forth moving mechanism 6 can be protected from being damaged.

In the automatic suction and collection of samples, if the test tube 12 puts a lid on it, if the test tube 12 or the washing spit 13 does not correspond in relative position to the pipette 1 lowered, or if the pipette 1 is not held in a vertical position, the first sensor 7 can detect a small external force to stop the movement of the pipette 1. Thus, possible malfunction that the pipette 1 may hit the test tube 12 or the washing spit 13 at some part thereof including the mouth or the side wall, so that it fails to go into the test tube 12 or the washing spit 13 in the normal manner or may be bent, or washing liquid may be spilled out from the washing spit 13 can be avoided.

In the manual suction and collection of samples, when the arm 2 is drawn back from the front stopping position to the rear stopping position through the front opening 10 after completion of sample sucking operation, even if an operator fails to lower the test tube 12 to draw it out from the pipette 1 timely, a possible risk that the test tube 12 and his/her hand holding it may be drawn together into the device D via the pipette 1 can be avoided.

What is claimed is:

1. A sample sucking device comprising:
   a pipette for sucking and collecting liquid samples;
   a sample sucking mechanism connected to the pipette;
   an arm, extending in a front direction and pivotally supported at a rear portion or an approximately intermediate portion thereof by a horizontal shaft, for holding the pipette substantially vertically at a front portion thereof;
   an arm holder for supporting the arm substantially horizontally so that the arm is pivotable in an up-and-down direction;
   an up-and-down moving mechanism for moving the arm holder in an up-and-down direction;
   a back-and-forth moving mechanism for moving the arm holder back and forth;
   at least two sensors, provided on the arm holder, in which a first sensor has a first preset value and a second sensor has a second preset value larger than the first preset value, for detecting an abnormal external force exceeding the respective preset value when exerted on the pipette or the arm; and
   a control section capable of selectively receiving an abnormality detection signal from each sensor, for controlling actions of the sample sucking mechanism, the up-and-down moving mechanism, and the back-and-forth moving mechanism, and issuing a moving action stop command to the up-and-down moving mechanism or the back-and-forth moving mechanism when a sensor selectively detects the respective abnormal external force.

2. The sample sucking device according to claim 1, wherein the up-and-down moving mechanism comprises an elevating belt mounted on the arm holder and stretching between an upper pulley and a lower pulley, and a motor for driving one of the pulleys rotatively.

3. The sample sucking device according to claim 1, wherein the back-and-forth moving mechanism includes an air cylinder, with the longitudinal axes thereof being oriented in a front direction, and a compressed-air supplying solenoid valve for driving a piston of the air cylinder forward and backward.

4. The sample sucking device according to claim 1 further comprising a visible alarm for indicating the abnormal external force exerted on the pipette or arm,
   wherein, upon receiving the abnormality detection signal from the first sensor, the control section is capable of issuing a moving action stop command to the up-and-down moving mechanism, together with a command to the visible alarm.

5. The sample sucking device according to claim 4, wherein the visible alarm is an LED lamp.

6. The sample sucking device according to claim 1 further comprising a visible alarm for indicating the abnormal external force exerted on the pipette or arm,
   wherein, upon receiving the abnormality detection signal from the second sensor, the control section is capable of issuing a moving action stop command to the back-and-forth moving mechanism, together with a command to the visible alarm.

7. The sample sucking device according to claim 6, wherein the visible alarm is an LED lamp.

8. The sample sucking device according to claim 1, further comprising an audible alarm for indicating the abnormal external force exerted on the pipette or arm,
   wherein, upon receiving the abnormality detection signal from the first sensor, the control section is capable of issuing a moving action stop command to the up-and-down moving mechanism, together with a command to the audible alarm.

9. The sample sucking device according to claim 8, wherein the visible alarm is a buzzer.

10. The sample sucking device according to claim 1, further comprising an audible alarm for indicating the abnormal external force exerted on the pipette or arm,
    wherein, upon receiving the abnormality detection signal from the second sensor, the control section is capable of issuing a moving action stop command to the back-and-forth moving mechanism, together with a command to the audible alarm.

11. The sample sucking device according to claim 10, wherein the visible alarm is a buzzer.

12. The sample sucking device according to claim 1, further comprising an urging mechanism interposed between the arm and arm holder, for urging the arm and arm holder to be drawn together,
    wherein the first sensor is a sensor which is switched by the arm being pivoted at a rotation angle exceeding a preset rotation angle against the urging mechanism when an abnormal external force exceeding the first preset value is exerted on the pipette or the arm, and wherein the second sensor is a sensor which is switched by the arm being pivoted at a rotation angle exceeding the preset rotation angle against the urging mechanism when an abnormal external force exceeding the second preset value is exerted on the pipette or the arm.

13. The sample sucking device according to claim 12, wherein the urging mechanism is a coiled tension spring having a predetermined urging force.

14. The sample sucking device according to claim 12, wherein each of the first sensor and the second sensor is a micro switch mounted on the arm holder.

15. The sample sucking device according to claim 12, wherein each of the first sensor and the second sensor is a photo interrupter mounted on the arm holder.

16. The sample sucking device according to claim 1, further comprising a washing mechanism for washing the pipette, wherein the control section is capable of issuing a command to the washing mechanism to wash the pipette.

17. The sample sucking device according to claim 16, wherein the control section is capable of issuing an additional command to stop further actions on suction of the sample and washing of the pipette after having given the moving action stop command to the up-and-down moving mechanism or the back-and-forth moving mechanism.

18. A sample sucking device according to claim 1, further comprising a sucking operation selection switch which selectively switches between an automatic sucking mode and a manual sucking mode.

* * * * *